(12) United States Patent
Guo

(10) Patent No.: US 8,465,450 B2
(45) Date of Patent: Jun. 18, 2013

(54) SUCTION DEVICE FOR PISTON BREAST PUMP

(75) Inventor: Paul Wen Guo, Shenzhen (CN)

(73) Assignee: Shenzhen Siyong Technology Ltd., Shenzhen, Guangdong (CN)

(\*) Notice: Subject to any disclaimer, the term of this patent is extended or adjusted under 35 U.S.C. 154(b) by 0 days.

(21) Appl. No.: 13/377,821

(22) PCT Filed: Feb. 4, 2010

(86) PCT No.: PCT/CN2010/070516
§ 371 (c)(1),
(2), (4) Date: Dec. 12, 2011

(87) PCT Pub. No.: WO2010/145217
PCT Pub. Date: Dec. 23, 2010

(65) Prior Publication Data
US 2012/0089087 A1    Apr. 12, 2012

(30) Foreign Application Priority Data
Jun. 18, 2009 (CN) ...................... 2009 2 0160877 U

(51) Int. Cl.
*A61M 1/06*    (2006.01)
(52) U.S. Cl.
USPC ............................................. 604/74; 604/73

(58) Field of Classification Search
USPC ...................................................... 604/73–76
See application file for complete search history.

(56) References Cited

U.S. PATENT DOCUMENTS

| 4,583,970 | A  | * | 4/1986  | Kirchner ......................... 604/74 |
| 5,406,859 | A  | * | 4/1995  | Belford ............................ 74/31 |
| 6,652,484 | B1 | * | 11/2003 | Hunckler et al. ............... 604/74 |
| 7,530,976 | B2 | * | 5/2009  | MacMahon et al. .......... 604/508 |
| 7,824,363 | B2 | * | 11/2010 | Myers ............................ 604/74 |
| 2010/0258631 | A1 | * | 10/2010 | Rueblinger et al. ..... 235/462.48 |

\* cited by examiner

*Primary Examiner* — Nicholas Lucchesi
*Assistant Examiner* — Benjamin Koo
(74) *Attorney, Agent, or Firm* — Novoclaims Patent Services, LLC; Mei Lin Wong

(57) ABSTRACT

A vertically hand palm pressing suction device for a piston breast pump includes a casing and a piston suction member. The device is provided with a pressing handle, which goes through the casing and is fixedly connected with a gear shaft mounted on a base. A piston of the piston suction member is connected to a toothed rack. The pressing handle and the toothed rack are operatively connected through a gear member, wherein the connection converts up-and-down movement of the pressing handle into forth-and-back movement of the piston.

10 Claims, 5 Drawing Sheets

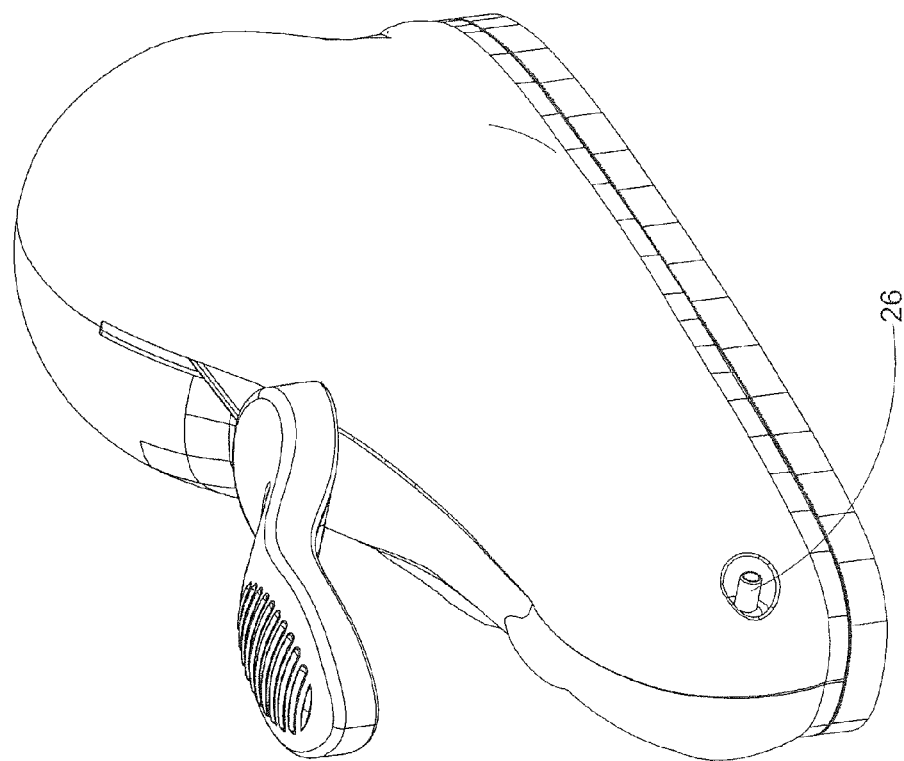

SUCTION DEVICE FOR PISTON BREAST PUMP

BACKGROUND OF THE PRESENT INVENTION

1. Field of Invention

The present invention relates to a breast pump for lactating women, and more particularly to a suction device in a piston-type breast pump.

2. Description of Related Arts

Manual breast pumps are divided into two types, the membrane type or the piston type. The membrane type has a simple structural construction and is easy to use. However, the drawbacks include a short stroke for the process, low suction force and requiring manual operation using fingers to providing pulling and pushing or squeezing force adequate for creating an vacuum condition and causing tiredness of users fingers. Piston-type breast pump has the advantages of greater stroke for the process, higher suction force and providing a relative closer simulation effect to a suction frequency of a baby. However, this type of breast pump also requires direct pulling and pushing and great pulling force is necessary which may cause tiredness of users fingers. After delivery, a mother will become very sensitive to tiredness of fingers and therefore a manual breast pump, which is of low frequency, high suction and high efficiency but does not require finger's operation for providing the pulling and pushing or squeezing force is needed.

SUMMARY OF THE PRESENT INVENTION

In view of the above, the present invention provides a suction device for a piston-type breast pump which is arranged for palm's pressing at a vertical direction.

Additional advantages and features of the invention will become apparent from the description which follows, and may be realized by means of the instrumentalities and combinations particular point out in the appended claims.

According to the present invention, the foregoing and other objects and advantages are attained by a breast pump with a piston suction arrangement, comprising a casing, a piston unit for providing suction, a base provided on the casing which comprises a gear shaft provided thereon, wherein the piston unit comprises a handle mounted to the base to secure into position and extended outside the casing arranged for pressing; wherein the piston unit comprises a cylinder member, a piston member, a toothed rack connected to the piston member, a gear unit operatively connected with the toothed rack and the handle such that the toothed rack and the handle are connected in a gear transmission manner through which a reciprocate movement of the handle at an up and down direction is changed into a reciprocate movement of the piston member at a back and forth direction.

The gear unit comprises a first gear mounted on an exterior end of the gear shaft, a second gear operatively connected to the first gear for serving as an intermediate gear, and a third gear having a diameter smaller than a diameter of the first gear and cooperatively connected to the first gear through the second gear by gear transmission, and a fourth gear having a diameter which is larger than the third gear coaxially positioned with the third gear while in gear connection with the toothed rack.

The third gear is rotatably supported by a third shaft member and a resilient member is provided on a protruded end portion of the third shaft member.

Preferably, serving as an improvement for the preferred embodiment, a roller unit engaged with a guiding groove of the toothed rack is farther provided, wherein the guiding groove is provided at a bottom end of the toothed rack such that the roller unit is guided to secure into position through the guiding groove of the toothed rack.

The base comprises a shaft support member defining a supporting side which has an inclined surface, and two gear shafts for the first gear and the fourth gear respectively, wherein the gear shaft for the first gear and the gear shaft for the fourth gear are sequentially aligned from an upper end towards as lower end of the inclined surface of the supporting side of the shaft support member along a direction of the handle.

The cylinder member of the piston unit has a rear end and comprises two connecting heads, namely a suction control head and an air passage head, at the rear end that are arranged for connecting to a control valve respectively.

Preferably, serving as an improvement for the preferred embodiment, the piston unit further comprises a control valve arrangement which comprises a control valve, an inlet, a tapered unit, a control shaft, a control core, an outlet and a control valve cavity, wherein the tapered unit is rotatably providing in the control valve cavity through a screw engagement in such a manner that the tapered unit is positioned between the inlet and the outlet and is arranged for providing a back and forth movement, which is driven by a rotational movement of the control shaft with which the control core is locked into position through an axial movement of the control shaft.

The control shaft further comprises a control head at one end of the control shaft which is extended outside the casing, thereby a user can control the control shaft outside the casing by using the control head.

Preferably, serving as an improvement for the preferred embodiment, two sealing plates are further provided. The casing has an opening through which the handle is extended outside the casing, the two sealing plates are extended from two sides of the handle at the opening of the casing, wherein a junction between the two sealing plates has a resilient thin wedge structure.

According to the preferred embodiment of the present invention, the suction pumping action of the a breast pump with a piston suction arrangement of the present invention has fundamentally changed the need of using fingers for pushing and pulling action or squeezing into a pressing action by using a palm, thereby an operation is enhanced. Since transmission or gear ratio can be increased by manipulating a transmission and diameter of gears through the gear transmission arrangement, an enhanced stroke of the piston unit can be obtained by pressing the handle using the palm at a small angle. Accordingly, a frequency requirement for the operation process is greatly reduced. Also, the provision of control valve makes it possible to adjust the level of suction force under a continuous manner.

Still further objects and advantages will become apparent from a consideration of the ensuing description and drawings.

These and other objectives, features, and advantages of the present invention will become apparent from the following detailed description, the accompanying drawings, and the appended claims.

BRIEF DESCRIPTION OF THE DRAWINGS

FIG. 5 is an illustration of a casing of the piston-type breast pump according to the above preferred embodiment of the present invention.

DETAILED DESCRIPTION OF THE PREFERRED EMBODIMENT

Further detailed description of the present invention is provided with the accompanying figures.

Figure 1:
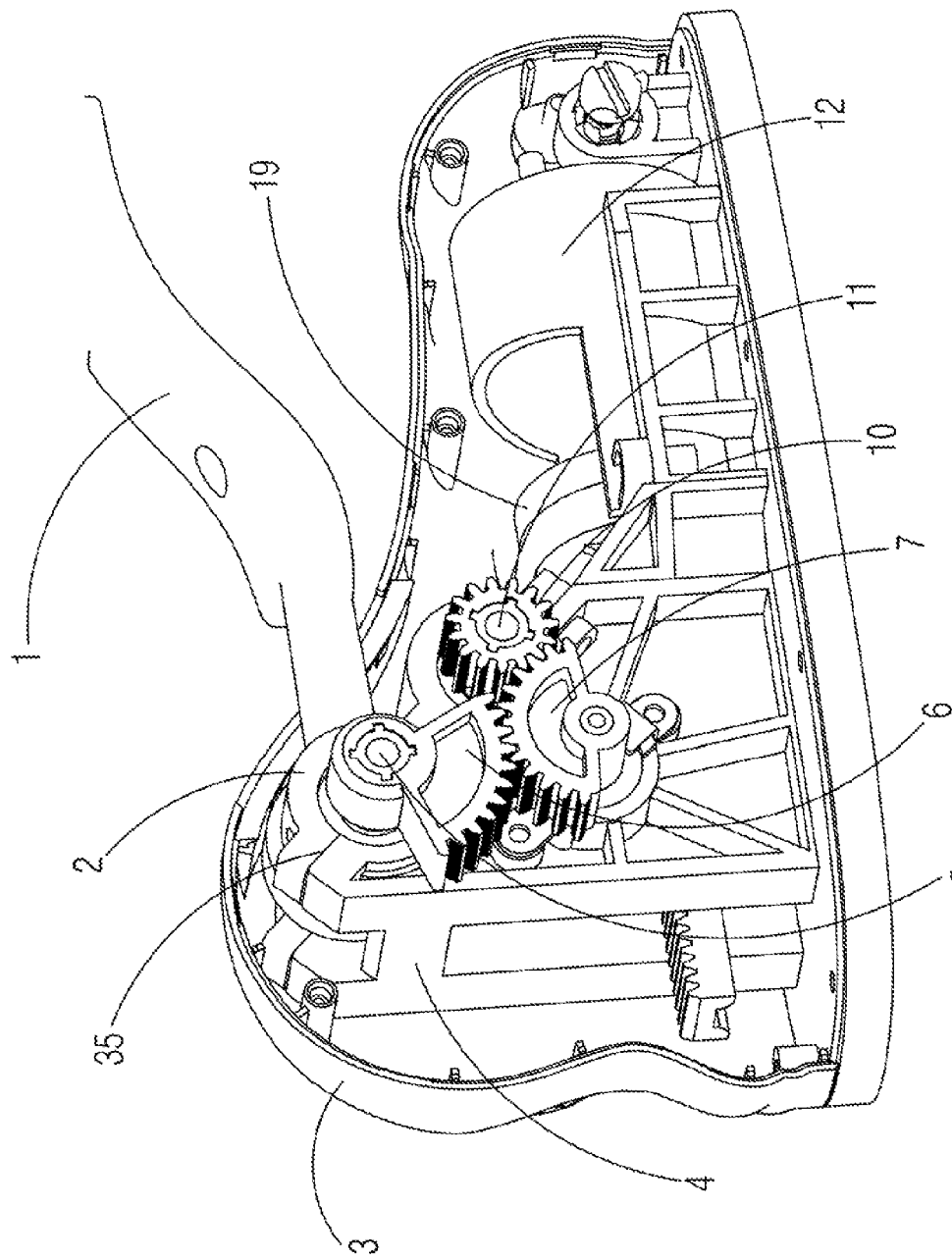
FIG. 1 is a front perspective view of a piston-type breast pump according to a preferred embodiment of the present invention.
Figure 2:
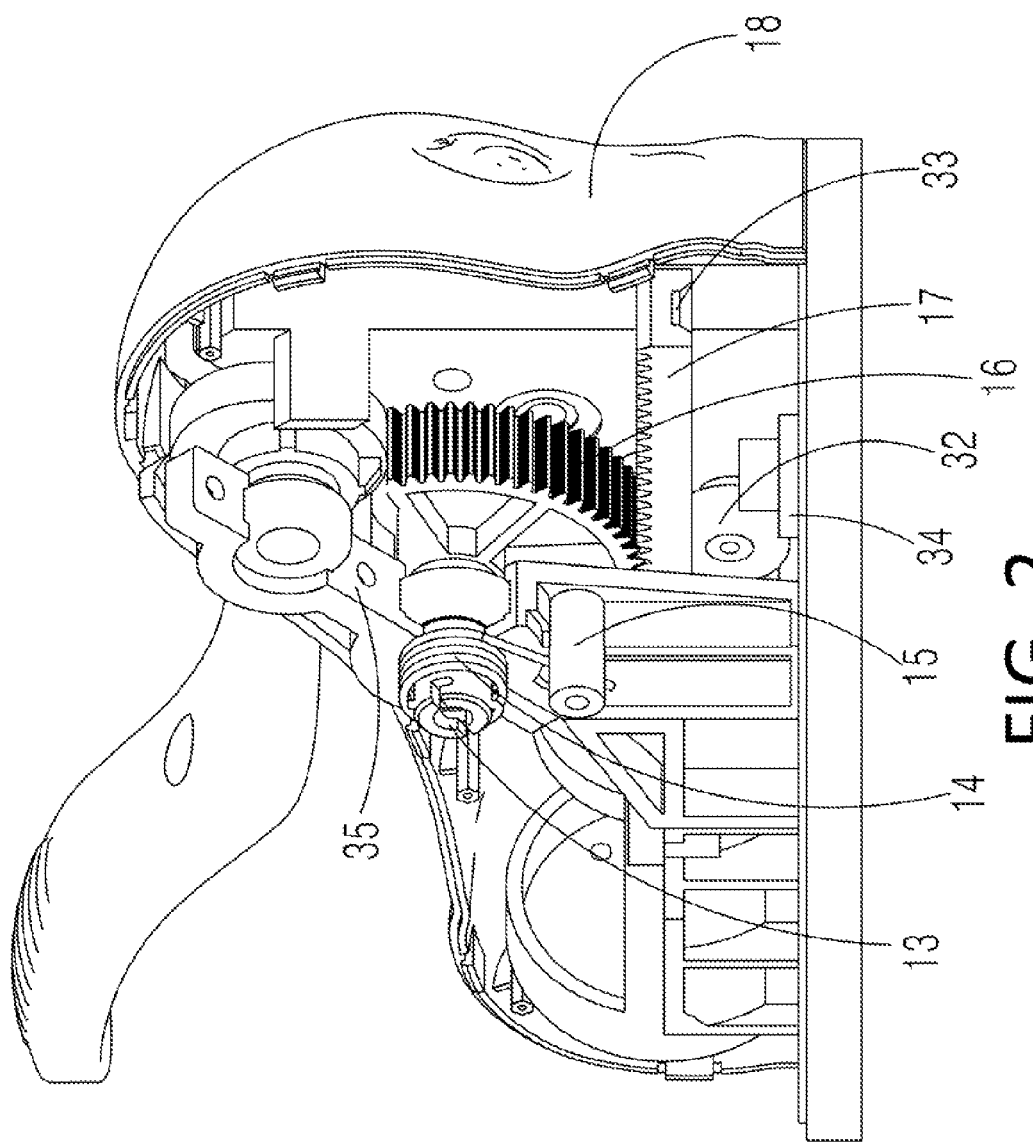
FIG. 2 is a rear perspective view of the piston-type breast pump according to the above preferred embodiment of the present invention.

Referring to FIGS. 1 and 2 of the drawings, a piston-type breast pump with a suction device according to a preferred embodiment of the present invention includes a casing 3, a piston suction member which is a piston unit for providing suction, a base 4 provided on the easing 3 and a gear shaft 5 provided on the base 4. The suction device comprises a handle 1, which is a pressing handle, mounted onto the gear shaft 5 of the base 4 to secure into position. The piston unit comprises a cylinder member 12, a piston member 19 and a toothed rack 17 which is connected to the piston member 19. A gear unit is further provided to connect between the handle 1 and the piston member 19 for providing transmission between the handle 1 and the piston member 19 in such a manner that a motion of the handle 1 at a first direction such as a vertically up and down motion is changed into a motion of the piston member 19 at a second direction such as a horizontally back and forth motion.

The gear unit according to the preferred embodiment of the present invention is further illustrated with the accompanying FIGS. 1 and 2 of the drawings. Preferably, the gear unit includes a first gear 6 mounted on an exterior end of the gear shaft 5 of the base 4, a second gear 7 serving as an intermediate gear, and a third gear 10 having a diameter smaller than a diameter of the first gear 6 which is initiated to rotate by the first gear 6 through the second gear 7. When the handle 1 is pressed to move up and down, the amplification ratio of angle of rotation is a ratio of the number of tooth of the first gear 6 to the number of tooth of the third gear 10. Accordingly, by pressing the handle 1 for a small angle of movement can result in an angle of rotation of the third gear 10 at an angle which is larger than the angle of movement of the handle 1. The second gear 7 is used to change a direction of movement.

Referring to FIGS. 1 and 2 of the drawings, a fourth gear 16 having a size larger than that of the third gear 10 is further provided and is coaxially connected with the third gear 10. The fourth gear 16 is engaged with the toothed rack 17 in such a manner that a rotational movement of the fourth gear 16 drives a movement of the toothed rack 17, which is a back and forth movement of the toothed rack 17, and then the movement of the toothed rack 17 drives a movement of the piston member 19, which is a back and forth movement of the piston member 19. The fourth gear 16 and the third gear 10, each defines an angle of rotation respectively, are moved to rotate under the same angle of rotation. A stroke amplification factor is a ratio of a diameter of the fourth gear 16 to a diameter of the third gear 10. Accordingly, the stroke is further amplified.

As shown in FIG. 2 of the drawings, the third gear 10 is rotatably connected to a third shaft member 11 which has a protruded end portion and a resilient member 14 provided at the protruded end portion of the shaft member 11 for serving as a spring member for return stroke. In particular, the base 4 preferably comprises a shaft support member defining a cylindrical protruded portion. The gear shaft 5 has a position groove 13 and the resilient member 14 has a first end and a second end. The resilient member 14 is secured into position through locking the first end with the cylindrical protruded portion of the shaft support member and positioning the second end into the position groove 13 of the gear shaft 5. Accordingly, the provision of the resilient member 14 enables the handle 1 and the piston member 19 to return to their original positions respectively, thereby speeding up an operation process of the device. The casing 3 has a truss construction and the third shaft member 11 further comprises a screw member 15 provided at a bottom end of the truss construction of the casing for stabilizing the truss construction of the casing 3.

According to the preferred embodiment of the present invention as shown in FIG. 2 of the drawings, the toothed rack 17 has a guiding groove 33 formed at a bottom end of the toothed rack 17. The base 4 is a shaft supporting frame which defines an inclined side and comprises a roller base 34 in the middle of the shaft supporting frame towards the inclined side of the shaft supporting frame. A roller unit 32 is further provided and positioned on the roller base 34 and is engaged with the guiding groove 33 such that a movement of the toothed rack 7 is guided to move in a precise manner and is firmly anchored and secured into position.

Referring to FIG. 1 of the drawings, the shaft support member of the base 4 defines a supporting side 35 which has an inclined surface, wherein the two gear shafts for the first gear 6 and the fourth gear 16 are aligned from an upper end towards a lower end along the inclined surface of the supporting side 35 at a direction of the handle 1. A double bear cover 2 is mounted onto the inclined surface. The inclined surface of the supporting side 35 of the shaft support member of the base 4 enables free movement of the handle 1 in which the handle 1 can be moved up and down without any obstacle or obstruction.

Figure 3:
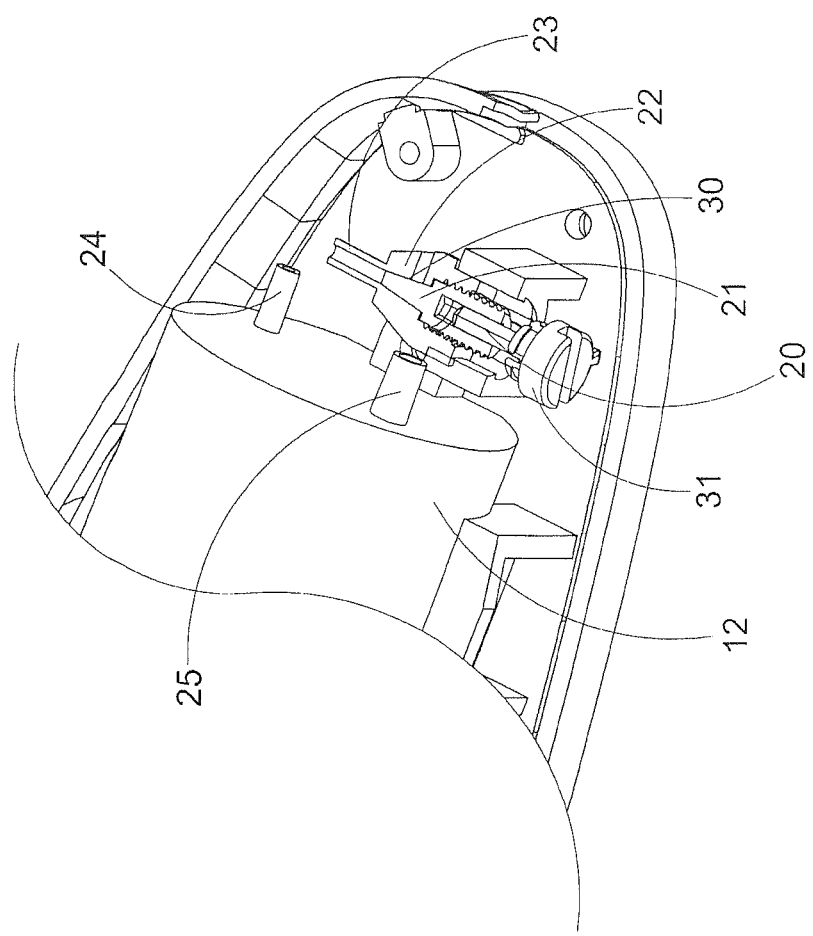
FIG. 3 is a perspective illustration of the piston-type breast pump which shows a rear end of a cylinder and a control valve according to the above preferred embodiment of the present invention.

Referring to FIG. 3 of the drawings, the cylinder member 12 of the piston unit has as rear end and comprises two connecting heads, namely a suction control head 24 and an air passage head 25. The tail end of suction head 21 is connected to a control valve 22. The air passage head 25 is an air output head which is outwardly extended to outside for connecting to other accessories not belonging to the piston unit through an external outlet 26 which is provided on the casing as shown in FIG. 5 of the drawings.

The control valve 22 is arranged for controlling a suction level of the piston unit which includes an inlet 23, as tapered unit 30, a control shaft 20, a control core 21, an outlet and a control valve cavity. The tapered unit 30 is rotatably provided in the control valve cavity through a screw engagement in such a manner that the tapered unit 30 is positioned between the inlet 23 and the outlet and is capable of having a back and forth movement driven by a rotational movement of the control shaft 20 with which the control core 21 is locking into position such that the control shaft is capable of movement along an axis. Preferably, in order to provide convenience to as user, the control shaft 20 further comprises a control head 31 at one end which extends outside the casing 3. During an operation, when a large suction force is required, the control head 31 is rotated to drive the control shaft such that the control core 21 is propelled forward and therefore the tapered unit 30 is moved forward. Accordingly, a flow rate of air between the inlet 23 and the outlet is decreased, a vacuum condition is enhanced and the suction force is increased. When the suction force is decreased, a reverse process is required.

Figure 4:
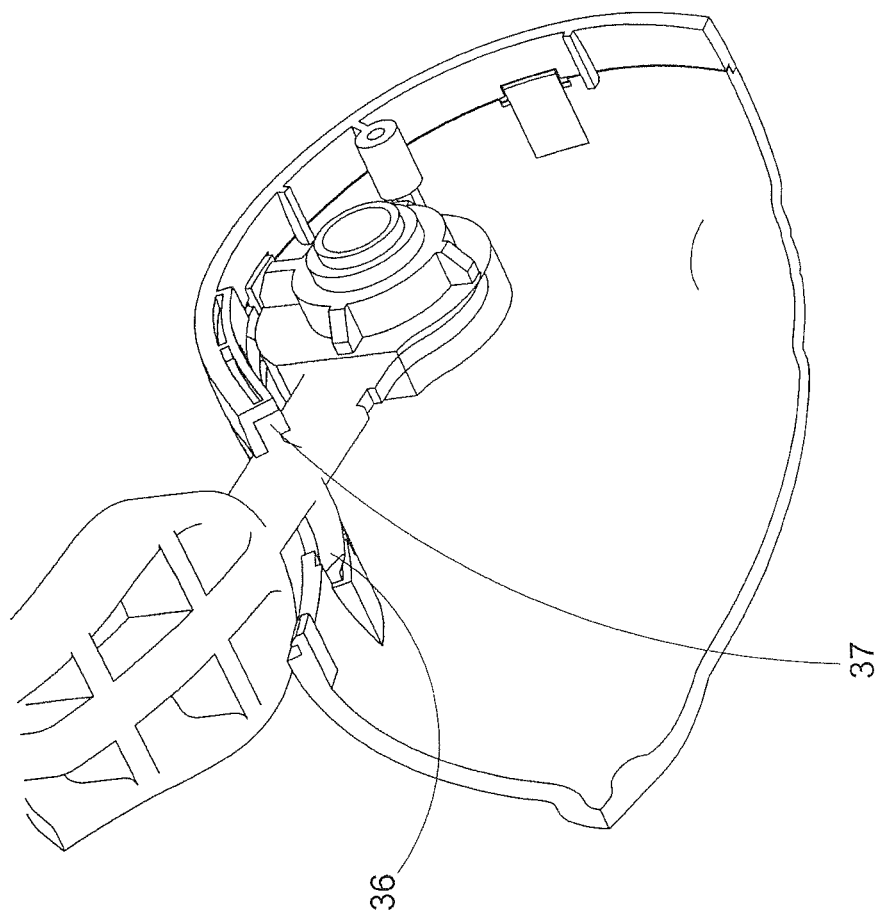
FIG. 4 is a perspective illustration of the piston-type breast pump for showing a handle from a bottom end according to the above preferred embodiment of the present invention.

In addition, according to the preferred embodiment as shown in FIG. 4 of the drawings, the casing 3 has an opening through which the handle 1 is extended and the handle 1 further comprises two sealing plates 36, 37 extended from two sides of the handle 1 at the opening of the casing 3. A junction between the two sealing plates 36, 37 is a resilient thin wedge structure. When the handle 1 is moved to the junction, the two sealing plates 36, 37 are caused to expose the opening of the casing 3. After the handle 1 passes the junction, the two sealing plates 36, 37 are returned to their original positions to close the opening of the casing 3.

It is possible to change the properties of the gear units according to the preferred embodiment of the present invention without departure from the principles of the present invention. For example, a size or a shape of the gears of the gear unit and the toothed rack, the number of gears and or the position of the gears can be substituted or changed without departure from the principles of the present invention.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

The invention claimed is:

1. A breast pump with a piston suction arrangement, comprising:
   a casing (3);
   a base (4) provided on said casing and comprises a gear shaft (5) provided thereon;
   a piston unit for providing suction, and comprises:
   a handle (1) mounted to said base and extended outside said casing and arranged for pressing;
   a cylinder member (12);
   a piston member (19);
   a toothed member (17) connected to said piton member; and
   a gear unit operatively connected with said toothed member (17) and said handle (1) such that said toothed member and said handle are connected such that a reciprocating movement of said handle in an up and down direction is changed into a reciprocate movement of said piston member at a back and forth direction, wherein said gear unit comprises a first gear (6) mounted on an exterior end of said gear shaft (5), a second gear (7) operatively connected to said first gear for serving as an intermediate gear, and a third gear (10) having a diameter smaller than a diameter of said first gear and cooperatively connected to said first gear through said second gear by gear transmission, and a fourth gear (17) having a diameter which is larger than said third gear coaxially positioned with said third gear while in gear connection with said toothed member (17); and
   a third shaft member rotatably supporting said third gear (10) and as resilient member (14) provided on a protruded end portion or said third shaft member.

2. The breast pump with a piston suction arrangement, as recited in claim 1, further comprising a roller unit (32) engaged with a guiding groove (33) of said toothed member (17), wherein said guiding groove is provided at a bottom end of said toothed member such that said roller unit is guided to secure into position through said guiding groove of said toothed member.

3. The breast pump with a piston suction arrangement, as recited in claim 2, wherein said base (4) comprises a shaft support member defining a supporting side (35) which has an inclined surface, and two gear shafts for said first gear and said fourth gear respectively, wherein said gear shaft for said first gear and said gear shaft for said fourth gear are sequentially aligned from an upper end towards a lower end of said inclined surface of said supporting side of said shaft support member along a direction of said handle.

4. The breast pump with a piston suction arrangement, as recited in claim 1, wherein said piston unit further comprises a control valve arrangement which comprises a control valve (22) an inlet (23), a tapered unit (30), control shaft (20), a control core (21), an outlet and a control valve cavity, wherein said tapered unit is rotatably providing in said control valve cavity through a screw engagement in such a manner that said tapered unit is positioned between said inlet and said outlet and is arranged for providing a back and forth movement, which is driven by a rotational movement of said control shaft with which said control core is locked into position through an axial movement of said control shaft.

5. The breast pump with a piston suction arrangement, as recited in claim 4, wherein said control shaft further comprises a control head (31) at one end of said control shaft which is extended outside said casing (3).

6. The breast pump with a piston suction arrangement, as recited in claim 1, further comprising two sealing plates (36, 37), wherein said casing has an opening through which said handle is extended outside said casing, said two sealing plates are extended from two sides of said handle at said opening of said casing, wherein a junction between said two sealing plates has a resilient thin wedge structure.

7. The breast pump with a piston suction arrangement, as recited in claim 2, further comprising two sealing plates (36, 37), wherein said casing has an opening through which said handle is extended outside said casing, said two sealing plates are extended from two sides of said handle at said opening of said casing, wherein a junction between said two sealing plates has a resilient thin wedge structure.

8. The breast pump with a piston suction arrangement, as recited in claim 3, further comprising two sealing plates (36, 37), wherein said casing has an opening through which said handle is extended outside said casing, said two sealing plates are extended front two sides of said handle at said opening of said casing, wherein a junction between said two sealing plates has a resilient thin wedge structure.

9. The breast pump with a piston suction arrangement, as recited in claim 4, further comprising two sealing plates (36, 37), wherein said casing has an opening through which said handle is extended outside said casing, said two sealing plates are extended from two sides of said handle at said opening of said casing, wherein a junction between said two sealing plates has a resilient thin wedge structure.

10. The breast pump with a piston suction arrangement, as recited in claim 5, further comprising two sealing plates (36, 37), wherein said casing has an opening through which said handle is extended outside said casing, said two sealing plates are extended from two sides of said handle at said opening of said casing, wherein a junction between said two sealing plates has a resilient thin wedge structure.

* * * * *